United States Patent [19]

Grey

[11] Patent Number: 5,760,254
[45] Date of Patent: Jun. 2, 1998

[54] PRODUCTION OF OXIRANE COMPOUNDS

[75] Inventor: Roger A. Grey, West Chester, Pa.

[73] Assignee: Arco Chemical Technology, L.P., Greenville, Del.

[21] Appl. No.: 683,355

[22] Filed: Jul. 18, 1996

[51] Int. Cl.$^6$ .................................................. C07D 301/06
[52] U.S. Cl. ............................................................. 549/532
[58] Field of Search ............................................. 549/532

[56] References Cited

U.S. PATENT DOCUMENTS 3,351,635 11/1967 Kollar ................................. 260/348.5
4,994,587 2/1991 Notermann et al. ..................... 549/534

FOREIGN PATENT DOCUMENTS

| | | |
|---|---|---|
| 1282772 | 4/1991 | Canada . |
| 1286687 | 7/1991 | Canada . |
| 1286688 | 7/1991 | Canada . |
| 1286689 | 7/1991 | Canada . |
| 1582261 | 1/1981 | United Kingdom . |

*Primary Examiner*—Ba K. Trinh
*Attorney, Agent, or Firm*—Stephen D. Harper; William C. Long

[57] ABSTRACT

Oxirane compounds are produced by molecular oxygen oxidation of an olefin in the presence of a nitrogen oxide catalyst.

10 Claims, No Drawings

PRODUCTION OF OXIRANE COMPOUNDS

BACKGROUND OF THE INVENTION

1. Field of the Invention

The present invention relates to the production of oxirane compounds by molecular oxygen oxidation in the liquid phase in the presence of nitrogen oxide catalyst.

2. Description of the Prior Art

Ethylene oxide is produced commercially by the vapor phase silver catalyzed oxidation of ethylene with molecular oxygen.

Propylene oxide is produced commercially by the Oxirane process wherein propylene is reacted with organic hydroperoxide in the presence of a catalyst such as molybdenum or by the chlorohydrin process. U.S. Pat. No. 3,351,635 is illustrative of the former process.

Attempts have been made to apply the vapor phase silver catalyzed procedures to the oxidation of propylene to propylene oxide but selectivities and conversions have generally been unsatisfactory. In certain of such systems, nitric oxide has been used in the gaseous feedstream as an efficiency enhancing component together with a nitrate salt as an essential component of the silver catalyst. See for example, Canadian 1,286,687, 1,286,688, 1,286,689 and 1,282,772 as well as U.S. Pat. No. 4,994,587.

UK 1,582,261 describes the production of propylene oxide by contacting propylene and molecular oxygen in the presence of dinitrogen tetroxide in a chlorinated organic liquid medium at temperatures in the range 0° to 60° C. The dinitrogen tetroxide is used in amount of 4–12% by volume based on propylene plus oxygen and yields of propylene oxide of 0.5% to 1.3% based on dinitrogen tetroxide are reported.

BRIEF DESCRIPTION OF THE INVENTION

It has now been found that an oxirane compound such as propylene oxide can be produced by the reaction of the corresponding olefin with molecular oxygen in the liquid phase in the presence of catalytic amounts of a nitrogen oxide catalyst. Mild reaction conditions can be used.

DETAILED DESCRIPTION

The present invention is applicable generally to the oxidation of an olefin to the corresponding oxirane compound. Propylene oxide production by oxidation of propylene is especially preferred.

Generally, unsaturated materials which are epoxidized in accordance with the invention include substituted and unsubstituted aliphatic and alicyclic olefins which may be hydrocarbons or esters or alcohols or ketones or ethers of the like. Preferred compounds are those having from about 2 to 30 carbon atoms, and preferably at least 3 carbon atoms. Illustrative olefins are ethylene, propylene, normal butylene, isobutylene, the pentenes, the methyl pentenes, the normal hexenes, the octenes, the dodecenes, cyclohexenes, methyl cyclohexene, butadiene, styrene, methyl styrene, vinyl toluene, vinylcyclohexene, the phenyl cyclohexenes, and the like. Olefins having halogen, oxygen, sulfur and the like containing substituents can be used. Such substituted olefins are illustrated by allyl alcohol, methallyl alcohol, cyclohexenol, diallyl ether, methyl methacrylate, methyl oleate, methyl vinyl ketone, allyl chloride, and the like. In general, all olefinic materials epoxidized by method previously employed can be epoxidized in accordance with this process including olefinically unsaturated polymers having up to about several thousand carbon atoms. Illustrative olefins are linseed oil, olive oil, soybean oil, cottonseed oil, tall oil glycerides, castor oil, corn oil, butyl-polyglycol esters of unsaturated fatty acids, liquid or solid polybutadiene, polyisoprene, unsaturated copolymers of ethylene and propylene including terpolymers thereof with cyclopentadiene and the like.

The catalyst which is employed is an oxide of nitrogen such as $N_2O_4$ or $NO_2$. Generally, suitable amounts of the catalyst which are employed range from about $1\times10^{-6}$ to $1\times10^{-2}$ moles catalyst per mole of olefin although amounts outside this range can be used. Preferably the catalyst is used in amount of $1\times10^{-5}$ to $1\times10^{-3}$ moles catalyst per mole of olefin.

Relatively mild reaction conditions can be employed; illustrative temperatures range from about 80° to 160° C. Preferred temperatures are 90° C. and higher, eg. 90° to 160° C. and especially 90°–120° C. Pressures sufficient to maintain the liquid phase are used, e.g. 30 to 2000 psia.

Preferably, a solvent is employed which does not impede the reaction, the solvent generally comprises the major component of the reaction mixture. Nitrile solvents such as acetonitrile can be used. Other solvents include benzonitrile, acetone, tetrahydrofuran, dimethylformamide; chlorinated hydrocarbons such as 1,2 dichlorethane and chlorobenzene can be used. The dichloroethane is especially useful. Mixtures of halogenated hydrocarbons as additives with other solvents can be used and promote the reaction. When used as an additive, amounts of the halogenated hydrocarbons as low as 500 ppm enhance the reaction. Water should be avoided as it interferes with olefin oxide formation.

Oxygen or mixtures of oxygen and an inert gas such as nitrogen can be used. Generally the oxidizing gas will comprise about 1–100 vol % molecular oxygen, the remainder being inert gas such as nitrogen, helium, argon, and the like.

Continuous, batch or semi-batch procedures can be employed. Generally, in batch operation a solution comprised of the nitrogen oxide, solvent and olefin is charged to an autoclave and the autoclave is then pressured to a desired pressure with oxidant gas. After a predetermined reaction time, eg. one to 24 hours, usually with agitation, the resulting reaction liquid is worked up for product recovery by conventional procedures.

The following examples illustrate the invention.

A 100 mL stainless steel top stirred reactor was charged with acetonitrile (40 ml), $N_2O_4$ (28 mg, 0.3 millimoles) and propylene (10 grams, 238 millimoles) and pressured to 800 psig of with 14% oxygen in nitrogen. The reaction mixture was heated at 100° C. for 14 hrs. After cooling to 23° C., the gases were vented to a gas bag for GC analyses. The reaction mixture was charged to 400 psig with nitrogen and the gases were vented to another gas bag. The reactor was pressurized to 400 psig with nitrogen again and the gases vented to a gas bag. The liquid phase was weighed (30 grams) and analyzed by GC and LC. Table 1 below lists the products and the amounts obtained. It was found that about 2.3 millimoles of propylene oxide were produced per 0.3 millimoles of $N_2O_4$, the selectivity of propylene conversion to propylene oxide was 26%.

TABLE 1

| Product | Millimoles | % Selectivity[1] |
|---|---|---|
| Propylene Oxide | 2.3 | 26 |
| Acetone | 0.2 | 2.4 |
| Carbon Dioxide | 3.4 | 12.8 |
| Carbon Monoxide | 0.9 | 3.4 |
| Acetic Acid | 0.9 | 6.6 |
| Formic Acid | 1.7 | 6.4 |
| Methanol | 0.5 | 1.7 |
| Acrolein | 0.8 | 9.5 |
| Acetaldehyde | 1.9 | 14.2 |
| Allyl Alcohol | 0.2 | 1.8 |
| Isopropanol | 0.1 | 1.3 |
| Hydroxyacetone | 0.6 | 7.3 |
| Formaldehyde | 0.2 | 0.8 |
| Propylene Glycol | 0.4 | 5.0 |

[1]Selectivity = (millimoles of product × number of carbons in product/number of carbons in propylene)/(THE SUM OF millimoles of all observed products × number of carbons in each product/number of carbons in propylene)

The above results demonstrate the catalytic production of propylene oxide by the process of the invention. In this example, nearly 8 millimoles of propylene oxide were formed per millimole of $N_2O_4$. When compared to the production of less than 0.2 millimoles of propylene oxide per millimole of $N_2O_4$ reported in UK 1,582,261, the advantages of the catalytic process of the invention are evident.

A series of additional examples were carried out, one of which was comparative, illustrating the effects of various solvents, additives and reaction temperatures by the same general procedure.

The catalyst in each case except Run 1 was $N_2O_4$; in Runs 2–7,9 and 10, 0.3 millimoles of $N_2O_4$ were used, in Run 8, 0.18 millimoles of $N_2O_4$ were used. Solvent, additives, reaction temperature and propylene oxide production are shown in the following Table 2.

TABLE 2

| EX# | Solvent | Additive[1] | Temp (°C.) | PO[5] Millimoles | % PO[5] Selectivity |
|---|---|---|---|---|---|
| 1[2] | Acetonitrile | None | 100 | Trace | — |
| 2 | Acetonitrile | None | 120 | 2.0 | 25 |
| 3 | Acetonitrile | DCE[3] | 100 | 2.3 | 27 |
| 4 | Acetonitrile | DCE[3] | 120 | 2.3 | 29 |
| 5 | Acetonitrile | Ethyl Bromide | 100 | 2.4 | 29 |
| 6 | Acetonitrile | Methyl Iodide | 100 | 1.3 | 20 |
| 7 | DCE[3] | None | 100 | 2.9 | 35 |
| 8[4] | DCE[3] | None | 100 | 2.5 | 31 |
| 9 | Chlorobenzene | None | 100 | 1.6 | 26 |
| 10 | Acetonitrile | None | 80 | 0.01 | 1 |

[1]Additive = 1 millimole
[2]Comparative run with no $N_2O_4$
[3]DCE = 1,2-Dichloroethane
[4]0.18 millimoles of $N_2O_4$
[5]PO = propylene oxide In non-catalytic comparative Run 1, essentially no propylene oxide was formed. Runs 2–9 show good results with various solvents and with various halogenated additives. Run 10 shows that at 80° C. reaction temperature, only a slight reaction is achieved.

In Run 8, nearly 14 millimoles of propylene oxide were formed per millimole of $N_2O_4$ as compared with about 8 in Example 1 and less than 0.2 in UK 1,582,261. This illustrates the advantages of operating with the lower amounts of catalyst. Although millimoles of propylene oxide produced was down slightly in Run 8 as compared to Run 7, production per millimole of catalyst was significantly increased.

The data also demonstrates that improved results are achieved with the use of halogenated additives such as 1,2 dichloroethane and ethyl bromide.

I claim:

1. A liquid phase process for the production of an oxirane compound which comprises reacting an olefin in the absence of solid catalyst with molecular oxygen at 90°–160° C. in the presence of catalytic amounts of nitrogen oxide catalyst.

2. The process of claim 1 wherein the catalyst is $N_2O_4$.

3. The process of claim 1 wherein the catalyst is $NO_2$.

4. A liquid phase process for the production of propylene oxide which comprises reacting propylene with molecular oxygen at 90°–160° C. in the absence of solid catalyst in the presence of catalytic of amounts nitrogen oxide catalyst.

5. The process of claim 1 wherein the reaction is carried out in a solvent.

6. The process of claim 1 wherein 1, 2 dichlorethane solvent is employed.

7. The process of claim 5 wherein 1, 2 dichlorethane solvent is employed.

8. The process of claim 1 wherein the reaction is carried out at 90°–120° C.

9. The process of claim 1 wherein $1\times10^{-6}$ to $1\times10^{-2}$ millimoles of catalyst per millimole of olefin are used.

10. The process of claim 1 wherein $1\times10^{-5}$ to $1\times10^{-3}$ millimoles of catalyst per millimole of olefin are used.

* * * * *